(12) United States Patent
Nordhoff et al.

(10) Patent No.: US 7,557,245 B2
(45) Date of Patent: Jul. 7, 2009

(54) (METH)ACRYLIC ACID CRYSTAL AND PROCESS FOR PRODUCING AQUEOUS (METH)ACRYLIC ACID

(75) Inventors: Stefan Nordhoff, Recklinghausen (DE); Torsten Balduf, Marl (DE); Gunther Bub, Marl (DE); Roland Fornika, Dulmen (DE); Jurgen Mosler, Castrop-Rauxel (DE); Thomas Rathke, Mandeville, LA (US); Axel Kobus, Bochum (DE); Dennis Thong, Marl (DE)

(73) Assignee: Evonik Stockhausen GmbH, Krefeld (DE)

( * ) Notice: Subject to any disclaimer, the term of this patent is extended or adjusted under 35 U.S.C. 154(b) by 539 days.

(21) Appl. No.: 10/507,969

(22) PCT Filed: Mar. 17, 2003

(86) PCT No.: PCT/EP03/02753

§ 371 (c)(1),
(2), (4) Date: May 11, 2005

(87) PCT Pub. No.: WO03/078378

PCT Pub. Date: Sep. 25, 2003

(65) Prior Publication Data

US 2005/0222459 A1    Oct. 6, 2005

(30) Foreign Application Priority Data

Mar. 15, 2002   (DE) .................. 102 11 686

(51) Int. Cl.
C07C 51/42    (2006.01)

(52) U.S. Cl. .................................. 562/600

(58) Field of Classification Search ........... None
See application file for complete search history.

(56) References Cited

U.S. PATENT DOCUMENTS

| | | | |
|---|---|---|---|
| 4,408,079 A | 10/1983 | Merger et al. | |
| 4,496,770 A | 1/1985 | Duembgen et al. | |
| 4,705,624 A | 11/1987 | Thijssen | |
| 4,734,102 A | 3/1988 | Thijssen et al. | |
| 4,735,781 A | 4/1988 | Thijssen et al. | |
| 4,762,622 A | 8/1988 | Thijssen | |
| 4,780,568 A | 10/1988 | Pascoe | |
| 5,380,933 A | 1/1995 | Ushikubo et al. | |
| 5,463,121 A | 10/1995 | Sridhar | |
| 5,504,247 A | 4/1996 | Saxer et al. | |
| 6,241,101 B1 | 6/2001 | Roodenrijs | |
| 6,448,439 B1 | 9/2002 | Eck et al. | |
| 7,112,695 B2 * | 9/2006 | Eck et al. ............. | 562/600 |
| 2001/0020111 A1 | 9/2001 | Ueno et al. | |
| 2003/0060661 A1 | 3/2003 | Eck et al. | |
| 2003/0175159 A1 | 9/2003 | Heilek et al. | |
| 2004/0116741 A1 | 6/2004 | Nordhoff et al. | |

FOREIGN PATENT DOCUMENTS

| | | |
|---|---|---|
| CA | 2 282 492 A1 | 9/1998 |
| CN | 1275972 A | 12/2000 |
| DE | 4401405 A1 | 7/1995 |
| DE | 19740252 A1 | 3/1999 |
| DE | 19838845 A1 | 3/2000 |
| DE | 10017903 A1 | 10/2001 |
| DE | WO 01/77056 A1 * | 10/2001 |
| DE | 10036880 A1 | 2/2002 |
| DE | 10036881 A1 | 2/2002 |
| DE | 10039025 A1 | 2/2002 |
| DE | 10149353 A1 | 7/2002 |
| EP | 0058927 A1 | 9/1982 |
| EP | 0092097 B1 | 10/1983 |
| EP | 0097405 A1 | 1/1984 |
| EP | 0097405 B1 | 1/1984 |
| EP | 0193226 A1 | 9/1986 |
| EP | 0608838 A2 | 8/1994 |
| EP | 0616998 A1 | 9/1994 |
| EP | 1116709 A1 | 7/2001 |
| JP | 57095938 | 6/1982 |
| NL | 1007687 C | 6/1999 |
| WO | WO 98/40342 | 9/1998 |
| WO | WO 99/14181 | 3/1999 |

OTHER PUBLICATIONS

International Search Report completed on Jun. 11, 2003 in PCT/EP2003/002753.
International Preliminary Examination Report completed on Jul. 19, 2004 in PCT/EP2003/002753.

* cited by examiner

*Primary Examiner*—Paul A Zucker
(74) *Attorney, Agent, or Firm*—Smith Moore Leatherwood LLP

(57) ABSTRACT

The present invention relates to processes for purifying a composition containing (meth)acrylic acid, at least one impurity and water, wherein the composition has a water content in the range of 0.55 to 90, based on the composition, to form a purified phase containing (meth)acrylic acid and at least one impurity, wherein, in the purified phase, the quantity of at least one impurity is less than 7% by weight, based on (meth) acrylic acid in the purified phase.

8 Claims, 7 Drawing Sheets

(METH)ACRYLIC ACID CRYSTAL AND PROCESS FOR PRODUCING AQUEOUS (METH)ACRYLIC ACID

This application is a national stage application under 35 U.S.C. 371 of international application no. PCT/EP03/02753 filed Mar. 17, 2003, which is based on German Application no. DE 102 11 686.5, filed on Mar. 15, 2002, and claims priority thereto.

BACKGROUND OF THE INVENTION

The present invention relates to a process for purifying a composition containing (meth)acrylic acid, an apparatus for producing pure (meth)acrylic acid, an apparatus for polymerizing (meth)acrylic acid, (meth)acrylic acid and polymers obtainable by these processes, their use and substances containing them.

"(Meth)acrylic acid" is used in this text for compounds having the nomenclature names "methacrylic acid" and "acrylic acid". Of the two compounds, acrylic acid is preferred according to the present invention.

It is often desirable to work up (meth)acrylic acid to high purities of at least 99.9% by weight for their use in polymers. In the hygiene industry, for example, superabsorber polymers based on polyacrylates may contain specific by-products only below the detection limit.

Crystallization is mentioned as an alternative to the production of high-purity organic substances. The two particular processes, which are used industrially, are suspension crystallization and layer crystallization (Wintermantel et al, Chem. Ing. Tech. 1991, 63, 881-891; Steiner et al, Chem. Ing. Tech. 1985, 57, 91-102).

However, a crystallization step alone is often insufficient to remove by-products sufficiently well from the crystals as microinclusions of mother liquors or the incorporation of impurities at crystal defects, etc. cannot be ruled out under finite crystal growth conditions. The adhesion of mother liquor to the crystal can also impair the purity of the products.

For this reason, the crystals produced, particularly in the case of a crystal suspension, are frequently washed with washing fluids after separation from the mother liquor and/or the crystals are subjected, during layer or suspension crystallization, to an exudation process during which impurities of any type may optionally be depleted. A process of this type may be carried out continuously in what are known as wash columns. The dissertation by Poschmann (Zur Suspensionskristallisation organischer Schmelzen und Nachbehandlung der Kristalle durch Schwitzen und Waschen, Diss. Uni. Bremen, Shaker Verlag Aachen 1996) provides an overview.

EP 0616998 discloses a process for producing at least 99.9% by weight acrylic acid starting from previously purified product having an acrylic acid content of 97.771% by weight. The effect of purification is achieved by the cooperation of dynamic and static layer crystallization processes. What is known as falling film crystallization is adopted as the final means of crystallization. An apparatus of this type may only be operated discontinuously and necessitates complex apparatus and logistics and comparatively high-energy consumption owing to the many process cycles required to obtain the necessary purities.

It is disclosed in WO 99/14181, to crystallize crude (meth)acrylic acid for purification in a first step and to work it up in a second step, optionally using wash columns. The process disclosed therein starts directly with the condensation products of catalytic gaseous phase oxidation for the production of (meth)acrylic acid. With this process, it is disclosed that the mother liquor produced after washing and separating the crystals is recycled into the condensation stage. With this process, a product having a purity of 98.8816% by weight was obtained from 90.972% by weight acrylic acid. However, this is not sufficient for some industrial applications. For example, the content of inhibitors and aldehydes in the pure (meth)acrylic acid is a critical variable, which, if exceeded, may lead to drawbacks, for example in the subsequent polymerization process.

Nienrood et al have disclosed how acrylic acid may be well purified by suspension crystallization and subsequent treatment in a hydraulic wash column (so-called TNO process; Proc. Bremer International Workshop on Industrial Crystallization, Bremen, 1994, Ed.: J. Ulrich, p. 4-11; Purification Potential of Suspension Growth Melt Crystallization, Proc. 4th International Workshop on Crystal Growth of Organic Materials, Bremen, 1997, Ed.: J. Ulrich, Aachen Shaker Verlag, p. 139-145). The acrylic acid used in these experiments was obtained from Aldrich and had a purity of 99.75% by weight. It could be purified to a purity of 99.97% by weight by this process. However, the use of lower-purity, acrylic acid has not been disclosed.

With former processes for producing (meth)acrylic acid, the (meth)acrylic acid obtained in a (meth)acrylic acid reactor and subsequently dissolved in water in a quench absorber is usually subjected to a complex distillation process, which sometimes necessitates the use of entrainers such as toluene so that high degrees of purity are then obtained by a crystallization process. Distillation processes for (meth)acrylic acid have the drawback that the (meth)acrylic acid is exposed to heat during the distillation process, through which its properties change, for example due to partial (pre)polymerization.

BRIEF SUMMARY OF THE PRESENT INVENTION

The object of the present invention is generally to overcome the drawbacks of the prior art by providing appropriate technical teaching.

According to a further object of the present invention, a process for producing high-purity (meth)acrylic acid from an impure crude (meth)acrylic acid stream from a process for producing (meth)acrylic acid is provided. The process should be harmless to the (meth)acrylic acid, industrially practicable and therefore superior to processes of the prior art from an economic and ecological point of view. In this connection, an excellent purification capacity and compliance with stringent ecological and economic requirements should be mentioned in this connection.

A further object of the present invention is to provide an apparatus for producing high-purity (meth)acrylic acid, which allows the purification of impure (meth)acrylic acid to maximum purity with low energy consumption and uninterrupted, environmentally sound operation.

A further object of the present invention is to provide a process and an apparatus wherein the risk of uncontrolled polymerization of (meth)acrylic acid during the production and, in particular, during the purification of (meth)acrylic acid is reduced.

An object of the present invention is also to reduce the quantity of stabilizers required to stabilize the (meth)acrylic acid between production and further processing of the (meth)acrylic acid.

A further object is to provide a further use of the apparatus for producing the (meth)acrylic acid or one of its components in which the risk of undesirable, uncontrolled polymerization of the (meth)acrylic acid is slight.

A further object is to provide a process and an apparatus for producing aqueous solutions of (meth)acrylic acid, which is as pure as possible. This object stands against a background, in particular, where aqueous (meth)acrylic acids are often used in solution, suspension or emulsion polymerization during the production of (meth)acrylic acid-containing polymers. It is of particular interest here that the energy consumption associated with exchanges of solvent in the individual steps of synthesis from monomer synthesis to polymerization is kept as low as possible.

An additional object according to the invention is to provide an aqueous (meth)acrylic acid phase, which has a comparably high water concentration at as high a purity of (meth)acrylic acid as possible. Aqueous acrylic acid phases of this type are in this respect advantageous because they can be used directly in the aqueous polymerization of absorbent polymers without a further dilution step. In this way, the until now common removal of water by distillation, followed by the purification of the acrylic acid and by a readdition of water for the polymerization of the water-absorbing polymer, is shortened by a step.

DETAILED DESCRIPTION OF THE PRESENT INVENTION

Figure 1:
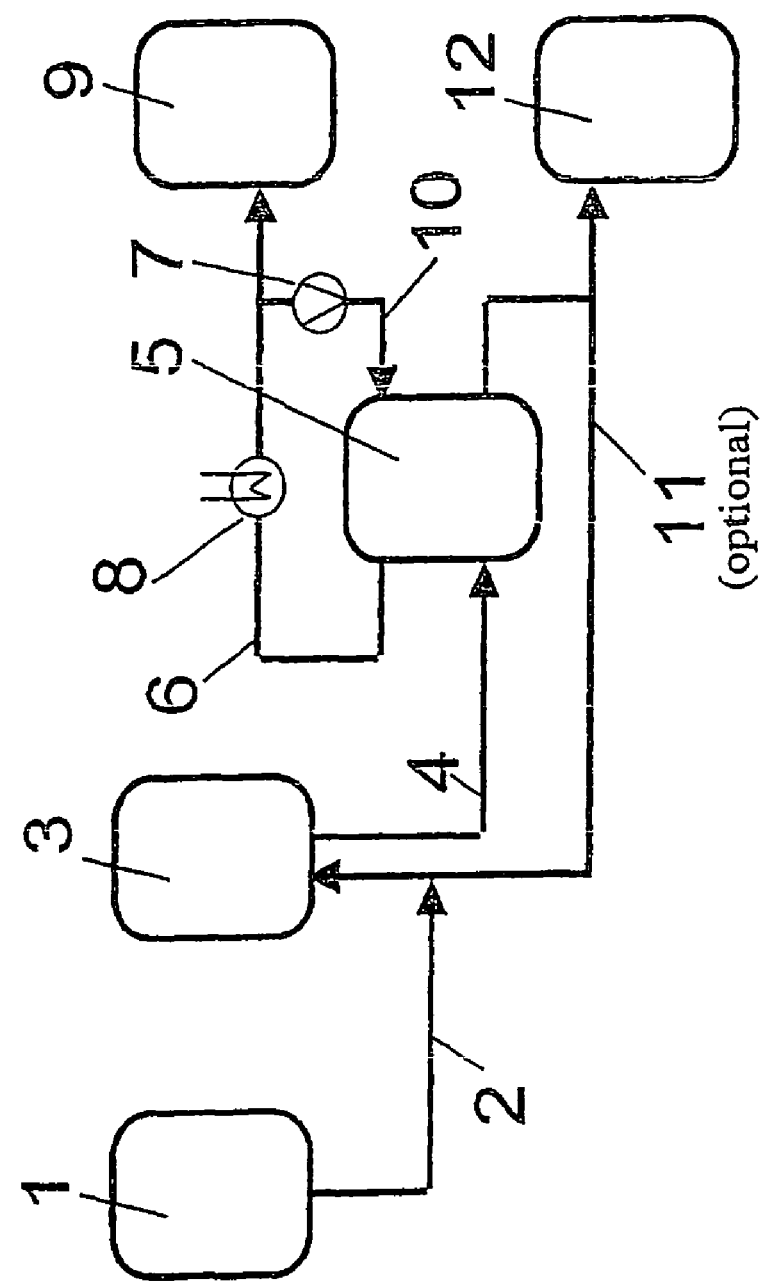
FIG. 1 is a further process diagram according to the present invention.

These objects are achieved with a process for purifying a composition containing (meth)acrylic acid, at least one impurity and water, wherein the composition has a water content in the range of about 0.55 to about 90, preferably about 7 to about 50 and particularly preferably about 10 to about 25, or also of about 10 to about 85, preferably of about 15 to about 80, particularly preferably about 25 to about 75% by weight, respectively based on the composition, to a purified phase containing (meth)acrylic acid and at least one impurity, wherein, in the purified phase, the quantity of at least one impurity is less than about 7% by weight, preferably less than about 5% by weight, more preferably less than about 3% by weight and particularly preferably less than about 1% by weight, based on the (meth)acrylic acid in the purified phase, comprising a stage of the process which includes the following process steps:

a) (meth)acrylic acid is crystallized from the composition while forming a suspension containing a mother liquor and (meth)acrylic acid crystals;

b) (meth)acrylic acid crystals are separated from the mother liquor;

c) at least a portion of the separated (meth)acrylic acid crystals is melted to form a melt; and d) a portion of the melt is recycled to step a) or step b), preferably step b), and wherein the portion of melt which is not recycled is in the form of a separated (meth)acrylic acid.

Provided that d) is not followed by further stages or steps of the process, the separated (meth)acrylic acid forms a component of the purified phase.

According to an embodiment of the process according to the present invention, the composition, as a composition which is rich in water, has a concentration of (meth)acrylic acid with up to about 10% by weight of impurities in the range of about 45 to about 80% by weight and water in the range of about 20 to about 55% by weight, based on the respective composition. The aqueous compositions may originate from a quench absorber. The aqueous compositions may also be a mother liquor depleted in (meth)acrylic acid or the filtrate from a crystallization, of which the (meth)acrylic acid is still to be purified.

In the case of the composition which is rich in water, the suspension formed in step a) preferably contains water crystals in addition to (meth)acrylic acid crystals. It is also preferred, if the melt contains about 10 to about 90% by weight, preferably about 15 to about 70% by weight and particularly preferably about 25 to about 55% by weight, based on the melt, of water in the case of the composition which is rich in water.

According to a further embodiment of the process according to the present invention, the composition, as a composition which is depleted in water, has a concentration of (meth)acrylic acid with up to about 10% by weight of impurities in the range of more than about 80% by weight and water in the range of less than about 20 to about 0.55% by weight, respectively based on the composition. These compositions which are depleted in water preferably originate from thermal depletion, preferably distillation, of (meth)acrylic acid or from a previous crystallization step which preferably corresponds to the process according to the invention.

In a further embodiment of the process according to the present invention, it is preferred if the purified phase, as a phase which is depleted in water, contains at least about 30% by weight, preferably at least about 55% by weight and particularly preferably at least about 75% by weight of (meth)acrylic acid and less than about 5% by weight, preferably less than about 2% by weight, particularly preferably less than about 1% by weight and more particularly preferably less than about 0.5% by weight of water, based on the respective purified phase.

In a further embodiment of the process according to the invention, it is preferred if the purified phase, as a phase which is rich in water, contains at least about 20% by weight, preferably at least about 30% by weight and particularly preferably at least about 70% by weight of (meth)acrylic acid and in the range of about 5 to about 80% by weight, preferably in the range of about 10 to about 70% by weight, particularly preferably in the range of about 15 to about 30% by weight of water, based on the respective purified phase.

The phase which is depleted in water may be supplied, for example, to a solvent-free polymerization process or a polymerization process in which the solvent is added only before or during the polymerization process. On the other hand, the phase which is rich in water may be added directly to a solution, suspension or emulsion polymerization process in which water is used as a solvent.

(Meth)acrylic acid may be obtained in the desired purities by appropriate combination of the process according to the invention, optionally in a plurality of stages.

For example, the (meth)acrylic acid obtained from the crystallization of an aqueous composition may be further purified as (meth)acrylic acid which is depleted in water. The mother liquor thus formed as an aqueous composition may be further processed to a phase which is depleted in water or is aqueous by the process according to the present invention.

With the process according to the present invention, it is preferred to crystallize (meth)acrylic acid in step a) at least in part, preferably to at least about 5% by weight, particularly preferably at least about 40% by weight and more preferably at least about 70% by weight of the crystals, to form a crystal with a crystal structure having a surface with at least one recess located on the surface, the crystal structure having an orthorhombic Bravais crystal lattice with an Ibam space group, crystallographic data a=about 9.952 A, b=about 11.767 A and c=about 6.206 A (cf. R. Boese, D. Blaser, I. Steller, R. Latz, A. Baumen Acta Crystallogr., Sect (Cr. Str. Comm.), 55, 9900006, 1999).

It is also preferred with the process according to the present invention if, in step a), the mother liquor comprises at least about 95% by weight of (meth)acrylic acid and water, the water concentration of the mother liquor being in the range of about 10 and about 90% by weight, in particular about 15 and about 70% by weight, preferably about 20 and about 40% by weight.

It is particularly preferred if the crystals have a tubular recess in their longitudinal direction, this recess preferably being dumb-bell-shaped, the openings of the tubular recess being greater on the end faces of the approximately square crystals than in the sectional face of the crystal lying parallel to the end faces.

It is also preferred with the process according to the invention if crystallization takes places in a suspension and not by the formation of layers in which a plurality of individual crystals are connected to one another to form a compact layer which is rigid in comparison with a crystal suspension. This is preferably achieved in that crystallization does not take place on a surface with corresponding temperature control—for example the wall of a layer crystallizer—with formation of a crystal layer. Instead, the crystals formed in the suspension are freely mobile in the liquid phase, such as the mother liquor, containing them.

The above-described recess advantageously complicates the inclusion of impurities such as mother liquor inside the crystal. The impurities are able to flow out or be washed out through the open recesses.

Even a high water content in the (meth)acrylic acid does not lead to an otherwise conventional increase in inclusions but to cavities which are open on both sides. If a water-containing suspension with such crystals is subjected to liquid/separation, the adhering mother liquor can advantageously flow away. This purification effect may be used, in particular, to considerably simplify the production of (meth)acrylic acid, to improve the quality of the (meth)acrylic acid produced in this way and thus to obtain pure, optionally aqueous (meth)acrylic acids.

Aqueous (meth)acrylic acids of which the water content is generally in the range of about 10 and about 90, preferably about 11 and about 50, particularly preferably about 12 to about 40% by weight and more particularly preferably of about 25 to about 35% by weight, based on the total quantity of water and (meth)acrylic acid, are produced by quenching the (meth)acrylic acid obtained by catalytic gaseous phase reaction with water in a quench absorber. In the past, water concentrations of this type had to be reduced almost completely in order to achieve sufficiently pure (meth)acrylic acid by crystallization. This necessitated, in particular, at least one distillation step which impaired the quality of the (meth)acrylic acid owing to incipient polymerization caused by exposure to heat.

In one embodiment, the volume of the recess is at least about 5% by volume, in particular at least about 10% by volume, preferably about 20% by volume, particularly preferably about 50% by volume, of the volume of the crystal. These large volumes of the recesses ensure that only comparatively few impurities can appear inside the crystal.

In a further embodiment of the present invention, the crystal comprises at least one inclusion, the sum of the volumes of inclusions being less than about 30% by volume, preferably less than about 15% by volume and particularly preferably less than about 5% by volume and more preferably less than about 1% by volume, of the volume of the crystal. Owing to the small volume of impure mother liquor in the inclusions, impurities which are unable to flow away or be removed by a washing process, in the (meth)acrylic acid, based on the volume of the crystal, are limited.

In a further embodiment, the crystal has a length of between about 0.001 and about 5 mm, in particular between about 0.05 and about 0.5 mm, preferably between about 0.1 and about 0.2 mm, on average. The length is determined by an image analysis system from about 500 crystals selected at random from photographs obtained using a light microscope. An image analysis system consisting of a light microscope with attached CCD camera and a PC evaluating unit is used for this purpose, whereby a PC programme from Soft Imaging System (SIS, V3.1) is employed.

The composition used in the process according to the invention, in particular for crystallizing a crystal according to the invention, is made up of at least about 60% by weight, preferably about 80% by weight and particularly preferably about 95% by weight of (meth)acrylic acid and water, the remainder being other substances, for example by-products produced during the synthesis of (meth)acrylic acid, wherein the water concentration is between about 0.5 and about 60% by weight, in particular between about 5 and about 40% by weight, preferably between about 15 and about 35% by weight.

This process surprisingly, but no less advantageously, leads to high-purity products which are also suitable for use in polymers, for example in the hygiene industry.

The process preferably takes place continuously. It is preferable to use a wash column to separate the (meth)acrylic acid crystals from the mother liquor. For this purpose, the wash column comprises a separating region in which the (meth)acrylic acid crystals are washed. For successful operation of a wash column, it is advantageous if the crystals to be washed are hard enough and have a specific narrow size distribution in order to guarantee appropriate porosity and stability of the resultant packed or unpacked filter bed.

It is also preferred that the process according to the present invention is characterised by a crystallization outlay (Wellinghof, Wintermantel, CIT 63 (1991) 9, p. 805, section 3.2.1) of about 1 to about 4.5, preferably less than about 1 to about 3.5 and particularly preferably of about 1 to about 2.5 and more preferably of about 1 to about 1.5.

The process according to the present invention may be carried out with impure crude (meth)acrylic acid containing less than about 99.5% by weight of (meth)acrylic acid. The crude (meth)acrylic acid used preferably has a purity of about 50% by weight to about 95% by weight, preferably about 75% by weight to about 90% by weight of (meth)acrylic acid.

More preferably, the condensed mixture of a catalytic gaseous phase oxidation for the production of (meth)acrylic acid may be introduced directly as a composition into the process according to the invention, preferably into step a).

Accordingly, (meth)acrylic acid, usually originating from a corresponding olefin, is generated in a reactor, then brought into an aqueous composition in a quench absorber, whereupon the (meth)acrylic acid may be distilled to a composition which is depleted in water in a distillation apparatus. The resultant crude (meth)acrylic acid stream is supplied to the purification apparatus. The process allows the production of very pure (meth)acrylic acid from comparatively impure crude (meth)acrylic acid.

Crystallizing agents which allow the purification process according to the invention to be carried out continuously should be used during crystallization. Suspension crystallization is preferably employed. This may be carried out advantageously in a stirred tank crystallizer, scraper crystallizer, cooling plate crystallizer, crystallizing worm, drum crystallizer, multitube crystallizer or the like. In particular, the variations of crystallization mentioned in WO 99/14181 may be used for this purpose. Crystallizers which may be operated continuously are again particularly advantageous. Cooling plate crystallizers or scraper coolers are preferred (Diss. Poschmann, p. 14). A scraper cooler is preferably used for crystallization.

In principle, any wash column which allows continuous implementation of the purification according to the present invention may be used for the process according to the present invention. With a conventional embodiment, the suspension in a hydraulic wash column is introduced in the upper part of the column; the mother liquor is removed from the column via a filter so that a close-packed crystal bed is formed. The crystal bed is permeated by the mother liquor in the direction of the base of the column and pressed downward by the fluid resistance. On the base of the column is a moving, preferably rotating, scraping device or scraper which produces a suspension again from the close-packed crystal bed and the washing melt introduced at the lower part of the wash column. This suspension is preferably pumped through a melter, preferably a heat exchanger, and melted. A portion of the melt may be used, for example, as washing melt; this is then recirculated into the column and preferably washes out the crystal bed which is migrating in the opposite direction, i.e. the crystallized (meth)acrylic acid is washed in the counter current of the recycled (meth)acrylic acid. On the one hand, the washing melt brings about washing of the crystals, on the other hand, the melt crystallizes at least in part onto the crystals. The liberated crystallization enthalpy heats the crystal bed in the washing region of the column. A purification effect similar to the exudation of the crystals is thus achieved. On the one hand, purification is therefore brought about by washing the surface of the (meth)acrylic acid crystals with molten, and therefore already purified, (meth)acrylic acid and, on the other hand, healing or exudation of impurities is achieved by crystallization of the molten purified (meth)acrylic acid on the existing (meth)acrylic acid crystals. This allows production of high-purity (meth)acrylic acid.

In a specific embodiment of the process according to the invention, the return flow resulting from the recycling of the molten (meth)acrylic acid from step c) into step a) or into step b) is greater than a feed flow of the composition which is continuously supplied to step a) from the exterior.

In particular, the return flow is at least twice and preferably at least ten times as great as the feed flow. The great return flow ensures that the exposure of the (meth)acrylic acid to heat on the melter is reduced.

For inoculation of the (meth)acrylic acid to be crystallized, it is advantageous to supply the separated crystallized (meth)acrylic acid from step b) at least in part to step a). The recirculated (meth)acrylic acid crystals simplify crystal growth in step a) and therefore assist separation of the (meth)acrylic acid from the mother liquor. This is advantageous, particularly with an aqueous composition.

From the energy point of view, a single-stage purification process with a single stage of the process is particularly advantageous and therefore particularly preferred. However, a two-stage purification process may be appropriate under certain circumstances.

To increase the yield, it is expedient to recycle the mother liquor separated in step b) at least in part to step a). (Meth)acrylic acid which has remained in the mother liquor may therefore be further crystallized with appropriate spatial temperature profiles, preferably to the thermodynamic limit (for example eutectic).

In an advantageous group of embodiments, the process according to the present invention comprises at least two stages of the process, which each include steps a) to d), wherein at least one of the following features ($\alpha 1$) to ($\alpha 4$) is fulfilled:

($\alpha 1$) separated, in particular crystalline and/or molten, (meth)acrylic acid from a first stage of the process is supplied at least in part to a second stage of the process;

($\alpha 2$) separated, in particular crystalline and/or molten, (meth)acrylic acid from a second stage of the process is supplied at least in part to a first stage of the process;

($\alpha 3$) mother liquor, in particular mother liquor separated in step b), from a first stage of the process is supplied at least in part to a second stage of the process;

($\alpha 4$) mother liquor, in particular mother liquor separated in step b), from a second stage of the process is supplied at least in part to a first stage of the process.

From this group of advantageous embodiments with at least one of the features ($\alpha 1$) to ($\alpha 4$) of the invention, the embodiments in which at least one of the following features ($\beta 1$) and ($\beta 6$) is fulfilled, are preferred:

($\beta 1$) crystalline (meth)acrylic acid from the first stage of the process is supplied to at least one of steps a) and b) of the second stage of the process;

($\beta 2$) molten (meth)acrylic acid from the first stage of the process is supplied to at least one of steps a) and b) of the second stage of the process;

($\beta 3$) crystalline (meth)acrylic acid from the second stage of the process is supplied to at least one of steps a), b) and c) of the first stage of the process;

($\beta 4$) molten (meth)acrylic acid from the second stage of the process is supplied to at least one of steps a), b) and c) of the first stage of the process;

($\beta 5$) mother liquid separated in step b) from the first stage of the process is supplied at least in part to step a) of the second stage of the process;

($\beta 6$) mother liquid separated in step b) from the second stage of the process is supplied at least in part to step a) of the first stage of the process.

If the second or further stage of the process brings about additional purification of the (meth)acrylic acid, i.e. (meth)acrylic acid already purified in a first stage of the process is further purified in a second (further) stage of the process, the following embodiments from this group of preferred embodiments of the present invention are particularly preferred:

(1) for achieving high-purity (meth)acrylic acid, molten (meth)acrylic acid from the first stage of the process is supplied to step a) of the second stage of the process;

(2) for achieving high-purity (meth)acrylic acid, crystalline (meth)acrylic acid from the first stage of the process is supplied to step a) of the second stage of the process;

(3) to allow thorough washing of the (meth)acrylic acid crystals from the first stage, molten (meth)acrylic acid from the second stage of the process is supplied to step b) of the first stage of the process; or (4) in order to provide particularly pure seed crystals, crystalline (meth)acrylic acid from the second stage of the process is supplied to step a) of the first stage of the process.

A combination of the respective embodiments (1) or (2) with (3) is most particularly preferred.

If the second stage of the process is used to increase the yield, the following embodiments from the group of preferred embodiments of the invention are particularly preferred:

(1) crystalline (meth)acrylic acid from the first stage of the process is supplied to step a) of the second stage of the process as seed crystals for crystallization;

(2) to increase the yield, the mother liquor separated in step b) of the first stage of the process is supplied at least in part to step a) of the second stage of the process;

(3) to increase the purity, molten (meth)acrylic acid from the second step of the process is supplied to step a) of the first stage of the process; or (4) to minimise energy consumption, crystalline (meth) acrylic acid from the second step of the process is supplied to step a) of the first stage of the process.

A combination of embodiments (2) and (4) is most particularly preferred.

Advantageously, at least two stages of the process are provided in series. "In series" can refer both to the separated (meth)acrylic acid, i.e. to the crystalline or molten (meth) acrylic acid, and to the separated mother liquor.

It is also advantageous to nest at least two stages of the process with one another. As a result, the number of melters which are required for melting and consume a large amount of energy during operation as heat exchangers or heaters, is smaller than the number of stages. For example, a simple nesting of two stages of the process can lead to a saving of one melter. Operation therefore becomes much more cost efficient with an identical yield and identical purity.

The number of stages of the process is based on the purity and economic efficiency to be achieved by the process. The achievable purity of (meth)acrylic acid is limited by the thermodynamic limit (for example eutectic) for a crystallization capability of (meth)acrylic acid from the mother liquor.

A specific embodiment of the process according to the invention is characterised by the following features ($\gamma 1$) and ($\gamma 2$):

($\gamma 1$) crystallization of (meth)acrylic acid from an impure crude (meth)acrylic acid stream from a process of producing (meth)acrylic acid;

($\gamma 2$) separation of the (meth)acrylic acid crystals from the mother liquor using a wash column, wherein the mother liquor from step ($\gamma 2$) is recycled at least in part to step ($\gamma 1$), the crude (meth)acrylic acid stream having a purity of less than about 99.5% by weight of (meth)acrylic acid.

The apparatus according to the present invention for producing (meth)acrylic acid comprises as components which are connected to one another in a fluid-conveying manner, a (meth)acrylic acid synthesis unit, which preferably includes a (meth)acrylic acid reactor and a quench absorber, a distillation apparatus and a purification apparatus, the purification apparatus including an apparatus unit comprising features ($\delta 1$) to ($\delta 4$):

($\delta 1$) the apparatus unit comprises a crystallization region, a separating region, a melter and at least three guides;

($\delta 2$) the crystallization region is connected to the separating region by a first guide;

($\delta 3$) the separating region is connected to the melter by a second guide;

($\delta 4$) the melter is connected to the crystallization region by a third guide or to the separating region by a fourth guide;

wherein the purification apparatus comprises an inlet which guides a composition containing (meth)acrylic acid, at least one impurity and water, the composition having a water content in the range of about 0.55 to about 90, preferably of about 7 to about 50 and particularly preferably of about 10 to about 25% by weight, based on the composition.

According to the invention, the expression "in a fluid-conveying manner" means that gases or liquids, including suspensions, or mixtures thereof are guided through corresponding lines. In particular, pipes, pumps and the like may be used for this purpose.

Owing to the low degree of distillation, the (meth)acrylic acid produced in this way is treated particularly carefully, whereby its quality is improved. In addition, the pure aqueous (meth)acrylic acid obtained in this way may be used in solution, emulsion or suspension polymerization processes so that a detrimental exchange of solvent from identical or different solvents may be avoided, in contrast to conventional reaction control.

In an embodiment of the apparatus according to the invention, it is preferred if the (meth)acrylic acid synthesis unit and the purification apparatus are connected to one another without a distillation apparatus.

In a further embodiment of the apparatus according to the invention, it is preferred if the quench absorber and the purification apparatus are connected to one another without a distillation apparatus.

An apparatus for producing acrylic acid which is preferred according to the invention preferably has the following construction in the region comprising a (meth)acrylic acid reactor and a quench absorber during the synthesis of acrylic acid: propylene and optionally further inert gases such as nitrogen or combustion gases such as carbon dioxide, $CO_2$, or nitrogen oxides are fed into a first reactor for initial catalytic oxidation via an educt inlet which opens into the first reactor. The first reactor is connected by a further line to a second reactor into which the product of the first catalytic oxidation process from the first reactor is introduced for second catalytic oxidation. The acrylic acid-containing product of the second catalytic oxidation is fed via a line located between the second reactor and quench absorber to the lower half of the quench absorber. In the quench absorber, the product of second catalytic oxidation is brought into contact with water, the water being introduced into the quench absorber above the supply of the product of the second catalytic oxidation.

On the one hand, a first phase which contains acrylic acid and water is discharged from the quench absorber below the supply of the product of second catalytic oxidation. This first phase may be recycled into the quench absorber again at least in part above the supply of the product of second catalytic oxidation. The first phase not recycled into the quench absorber is supplied to the distillation apparatus and subjected, for example, to azeotropic separation during which the acrylic acid is concentrated and purified. A second phase which contains acrylic acid and water may be discharged from the quench absorber above the return of the first phase and below the introduction of water into the quench absorber. This second phase, like the first phase, may be supplied to the distillation apparatus and be subjected, for example, to azeotropic separation during which the acrylic acid is concentrated and purified. The exhaust gases discharged from the quench absorber may be supplied to a catalytic combustion process. The combustion gases from catalytic combustion may be introduced into the first reactor as inert gases. The water recovered during the concentration of acrylic acid may be recycled into the quench absorber. Further details of the production of acrylic acid are disclosed in DE 197 40 252 A1.

According to the invention, acrylic acid may also be synthesised in a synthesis unit which converts propane directly into acrylic acid. Acrylic acid may additionally be synthesised in aqueous reaction media, preferably as homogeneous catalysis. During a reaction in aqueous reaction media, the acrylic acid would be produced in the form of the composition which is rich in water without the need to add water in a quench absorber.

An apparatus for the production of (meth)acrylic acid which is preferred according to the invention comprises the (meth)acrylic acid reactor and a quench absorber during the synthesis of (meth)acrylic acid by catalytic gaseous phase reaction of C4 starting compounds with oxygen. (Meth) acrylic acid may be obtained particularly preferably by catalytic gaseous phase oxidation of isobutene, isobutane, tert.-butanol, iso-butyraldehyde, methacrolein or meth-tert.-butylether. Further details on the production of (meth)acrylic acid are disclosed in EP 0 092 097 B1, EP 0 058 927 and EP 0 608 838.

The purification apparatus is capable of obtaining very pure (meth)acrylic acid with degrees of purity over about 99.5% by weight from a comparatively impure crude (meth) acrylic acid stream containing approximately 85% by weight of (meth)acrylic acid. According to the present invention, it is possible efficiently to purify impure crude (meth)acrylic acid stream with about 50% by weight to about 95% by weight (meth)acrylic acid, preferably about 75% by weight to about 90% by weight (meth)acrylic acid. This effective purification allows preliminary purification of the crude (meth)acrylic acid stream using the distillation apparatus to be reduced, so the heat exposure of the (meth)acrylic acid is reduced. The quality of the (meth)acrylic acid is therefore improved.

The apparatus unit comprises a separate purification apparatus for a further increase in the purity of the (meth)acrylic acid. This separate purification apparatus may be used for the further purification of the end product, in particular for the further purification of the (meth)acrylic acid leaving the melter.

To improve crystallization, the separating region is preferably connected to the crystallization region by a first return for separated (meth)acrylic acid.

To increase the yield, the separating region is advantageously connected to the crystallization region by a second return for separated mother liquor.

In terms of energy, a single-stage purification apparatus with a single apparatus unit is basically particularly advantageous and therefore particularly preferred. However, a two-stage purification apparatus may be appropriate under certain circumstances.

To increase the efficacy of purification, in particular to increase the purity and yield, the apparatus according to the invention contains at least two apparatus units according to features ($\delta$1) to ($\delta$4), which are connected by at least one connecting line, the connecting line being a feed line or a return line and at least one of the following features ($\epsilon$1) to ($\epsilon$4) being fulfilled:

($\epsilon$1) the separating region of a first apparatus unit is connected via the connecting line to the crystallization region of a second apparatus unit;

($\epsilon$2) the melter of a first apparatus unit is connected via the connecting line to the crystallization region of a second apparatus unit;

($\epsilon$3) the separating region of a second apparatus unit is connected via the connecting line to the crystallization region of a first apparatus unit;

($\epsilon$4) the melter of a second apparatus unit is connected via the connecting line to the crystallization region of a first apparatus unit. The connecting lines may be a feed line as well as a return line.

For example, it is expedient with the process according to the invention to provide a feed line from the separating region of the first apparatus unit (first stage of the process) to the crystallization region of the second apparatus unit (second stage of the process) in order to increase the yield. A return between the separating region of the second stage and the crystallization region of the first stage, on the other hand, is expedient for the preparation of seed crystals.

Therefore, at least two apparatus units may advantageously be connected in series to improve the purity and yield.

The number of melters required and therefore the energy required to operate the apparatus may be reduced by nesting at least two apparatus units.

With the process according to the present invention for purifying acrylic acid, a temperature in the range of about −20 to about 20° C., preferably from about −10 to about 13° C. at a pressure of from about 1 to about 10 bar prevails in the separating region. It is preferred the temperature and pressure prevailing in the lower region of the separating region are lower than in the upper region of the separating region. Preferably, a temperature of from about −20 to < about 12° C. at a pressure of from about 1 to about 2 bar prevails in the lower region of the separating region. A temperature of at least about 12° C. at a pressure of from about 1 to about 10 bar, preferably from about 3 to about 7 bar prevails in the upper region of the separating region.

With the process according to the invention for purifying acrylic acid, a temperature in the range of from about −20 to about 20° C., preferably from about −12 to about 13° C. at a pressure of from about 0.5 to about 10 bar, preferably from about 0.8 to about 2 bar prevails in the crystallization region.

With the process according to the present invention for purifying acrylic acid, a temperature in the range of from about 10 to about 50° C., preferably from about 11 to about 30° C. at a pressure of from about 1 to about 10 bar, preferably from about 3 to about 7 bar prevails in the melter.

With the process according to the present invention for purifying methacrylic acid, a temperature in the range of from about −5 to about 30° C., preferably from about −3 to about 20° C. at a pressure of from about 1 to about 10 bar prevail in the separating region. It is preferred that the temperature and pressure prevailing in the lower region of the separating region are lower than in the upper region of the separating region. Preferably, a temperature of from about −16 to <about 15° C. at a pressure of from about 1 to about 2 bar prevails in the lower region of the separating region. A temperature of at least from about 15° C. and a pressure of about 1 to about 10 bar, prevail in the upper region of the separating region.

With the apparatus according to the invention for purifying methacrylic acid, a temperature in the range of from about −5 to about 30° C., preferably from about −3 to about 20° C. at a pressure of from about 1 to about 10 bar, preferably from about 1 to about 2 bar prevails in the crystallization region.

With the apparatus according to the invention for purifying methacrylic acid, a temperature in the range of from about 10 to about 50° C., preferably from about 11 to about 30° C. at a pressure of from about 1 to about 10 bar, preferably from about 3 to about 7 bar prevails in the melter.

The temperature and pressure conditions prevailing in the guides allow reliable, uninterrupted transport of the (meth) acrylic acid and the substances possibly accompanying it in these guides.

The apparatus according to the invention enables a relatively impure (meth)acrylic acid to be used as the starting material, so the preliminary expenditure for distillation of the (meth)acrylic acid originating from synthesis is reduced. Therefore, the exposure of the (meth)acrylic acid to heat, which may lead to undesirable polymerization, is reduced.

The invention further relates to an apparatus for polymerising (meth)acrylic acid, comprising an apparatus for producing (meth)acrylic acid and a polymerization unit, wherein the purification apparatus of the apparatus for producing (meth) acrylic acid is connected to the polymerization unit.

The invention also relates to a (meth)acrylic acid obtainable by the process of purification according to the present invention.

The present invention further relates to a process for producing a polymer containing (meth)acrylic acid, wherein a (meth)acrylic acid according to the present invention or a purified phase according to the invention, obtainable by the process of purification according to the invention, is polymerised. Polymerization preferably takes place as solution polymerization, reaction control in a recessed belt being particularly preferred. In the process, the aqueous phase is used directly or, alternatively, the phase which is depleted in water is correspondingly diluted. Polymerization generally takes place in a medium having a water content of about 20 to about 80% by volume, based on the medium.

The invention also relates to a polymer which may be obtained by the process described in the foregoing paragraph.

The polymer is preferably an absorbent polymer with a maximum absorption of about 0.9% by weight aqueous NaCl solution according to ERT 440.1-99 in a range of about 10 to about 1,000, preferably about 15 to about 500 and particularly preferably about 20 to about 300 ml/g. Further details about absorbent polymers and their production may be found in "Modern Superabsorbent Polymer Technology", Fredrick L. Buchholz, Andrew T. Graham, Whiley-VCH, 1998.

The fibers, shaped articles, films, foams, superabsorbent polymers or hygiene articles according to the invention are based at least on or contain at least the (meth)acrylic acid according to the invention or the polymer according to the invention.

The (meth)acrylic acid according to the invention or the polymer according to the invention is used in or for the production of fibers, shaped articles, films, foams, superabsorbent polymers or hygiene articles.

The apparatus according to the invention or the purification apparatus according to the invention or the process according to the invention is used for producing acrylic acid having a purity of more than about 90% by weight, preferably more than about 95% by weight and particularly preferably more than about 99.5% by weight, based on the respective (meth) acrylic acid with impurities.

In a specific embodiment of the process according to the invention for purifying (meth)acrylic acid, the process comprises two process steps γ1) crystallization of (meth)acrylic acid from an impure crude (meth)acrylic acid stream from a process of producing (meth)acrylic acid;

γ2) separation of the (meth)acrylic acid crystals from the mother liquor using a wash column, wherein the mother liquor from step (γ2) is recycled at least in part to step (γ1), the crude (meth)acrylic acid stream having a purity of less than about 99.5% by weight of (meth)acrylic acid.

A mechanically operated wash column (Diss. Poschmann, p. 18) is particularly preferred according to the present invention.

With a mechanical wash column—reference being made to EP 0 193 226 B and NL 100 76 87 A for example—a dense crystal bed is produced within the column by means of a piston which is permeable to the melt. The piston may be located at the upper or lower end of the column; in the first case, the suspension is supplied in the upper region of the column and in the second case in the central or lower region. The piston is permeable to the melt so, during compression, melt issues at the back of the piston, where it is removed. In a similar manner to a hydraulic wash column, the mechanical wash column also contains a scraping apparatus, for example a moving, preferably rotating, scraping member for scraping crystals from the crystal bed and transferring them into a suspension with the wash melt. The wash melt moves counter current to the crystal bed. Suspension is removed from the side of the wash column remote from the piston and, after the melting operation, a proportion of the melt may be recycled as wash melt and the remainder removed from the circuit as extra-pure product.

Embodiments of suspension crystallization with subsequent washing of the crystals in a hydraulic or mechanical wash column can be found in the book "Melt Crystallization Technology" by G. F. Arkenbout, Technomic Publishing Co. Inc., Lancaster-Basel (1995), p. 265-288 and the article about the preconcentration of waste water using the Niro freeze concentration process in Chemie Ingenieur Technik (72) (10/2000), 1231-1233.

Depending on the application, a washing fluid familiar to a person skilled in the art may be used as the washing fluid (for example water in the case aqueous solutions). For washing the crystallized (meth)acrylic acid, as already mentioned, it is most particularly preferred to use a proportion of the molten crystals thereof. This ensures, on the one hand, that no further substance has to be introduced into the system for the production of high-purity products and, on the other hand, the molten crystals are also used to force back the mother liquor front in the wash column and simultaneously have a purifying effect similar to exudation on the crystals. Products are not lost in the process as the washing fluid crystallizes again on the crystals to be washed and is therefore found in the product again (for example brochure from Niro Process Technology B.V., Crystallization and wash column separation set new standards in purity of chemical compounds).

It is further preferred in the process according to the present invention that the process occurs in a device according to the invention.

In an embodiment of the process according to the invention, the separated, in particular crystalline and/or molten, (meth)acrylic acid is purified in a separate purification process. For example, it is possible to treat the mother liquor from step b) before the return to step a), at least once by a further purification process. A person skilled in the art is sufficiently familiar with such processes. Preferably, the following processes in particular are employed:

1) Simple Distillation

Separation into low-boilers (acetic acid, water, etc.), medium-boilers ((meth)acrylic acid) and high-boilers (MSA, PTA, etc.). The purification of impure (meth) acrylic acid (in particular of water and acetic acid) is carried out in the majority of cases by azeotrope rectification. Entrainers such as toluene or MIBK, for example, are used (EP 0 695 736 B1).

2) Extraction of Acrylic Acid

The (meth)acrylic acid may be obtained by extraction with n-butanol. An aqueous phase in which the minor constituents are dissolved remains. The extraction of (meth) acrylic acid from impure solutions pertains to the prior art similarly to distillation.

(Meth)acrylic acid may also be extracted, for example, from aqueous solutions with liquid ion exchanges, mixtures of tri-n-alkylamines and aliphatic alcohols or n-butanol (Vogel et al.: Chem. Eng. Technol. 23 (2000) 1, pp. 70-74; Tamada et al.: in Solvent Extraction 1990, Ed.: T. Sekine, Elsevier Science Publishers B.V. pp. 1791-1796; JP 57 095 938; WO 98/40342; Information brochure from SULZER Chemtech on fractional extraction of (meth)acrylic acid with n-butanol).

3) Dewatering of (meth)acrylic Acid by Pervaporation

This process is disclosed inter alia in DE 4401405 A1.

Advantageously, the mother liquor from step b), prior to return to step a), may be treated at least once by a process including steps a) and b) and may be recycled to the respectively purer branched partial stream in step a) of the original process or a prior process so that maximum purity may be achieved with the minimum loss of yield.

Figure 2:
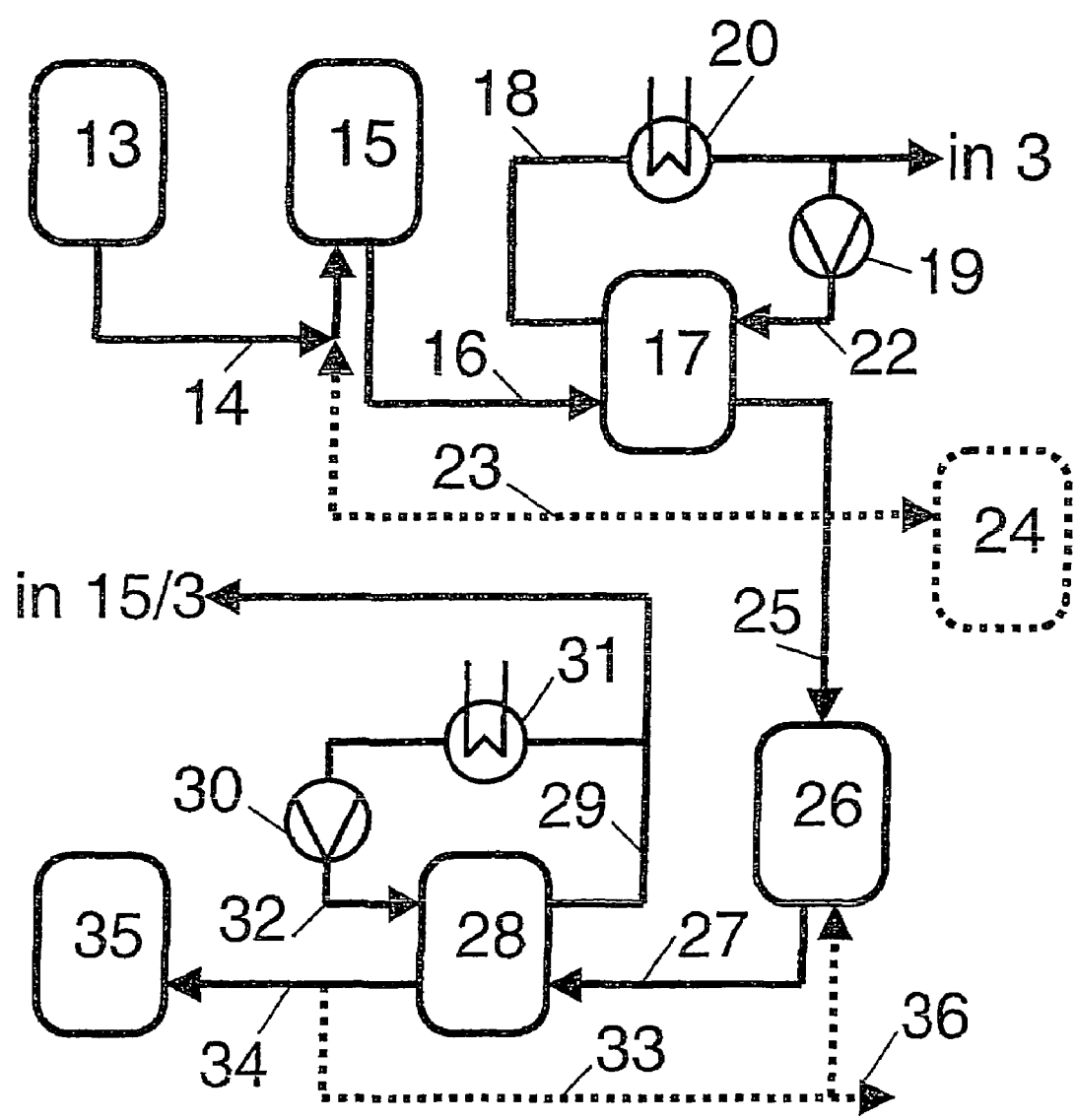
FIG. 2 is a process diagram according to the present invention with two process stages connected in series.

FIG. 2 illustrates this matter. The mother liquor from crystal separation in the wash column may also be treated in a subsequent crystallization region. The resultant suspension may then be worked-up in turn in a wash column as usual. The mother liquor now formed may be similarly treated in the following stages. There is a choice between recycling the respective purer streams produced by this procedure into crystallization of the first purification process or into crystallization of a prior process. Maximum purity can thus be achieved with a minimum of waste using relatively inexpensive apparatus.

The processes according to the invention may be carried out continuously and discontinuously, continuous operation being preferred as such operation is particularly cost effective.

The invention further relates to an apparatus for polymerising (meth)acrylic acid, comprising an apparatus according to the invention for producing (meth)acrylic acid and a polymerization unit, the purification apparatus of the apparatus for producing (meth)acrylic acid being connected to the polymerization unit. This polymerization unit may be a kneaded or stirred-tank reactor or a recessed belt in or on which polymerization takes place. Recessed belt polymerization is advantageous for the phase which is rich in water. The phase, which is rich in water, has a water and (meth)acrylic acid concentration, which is particularly suitable for the solution polymerization of polymers based on (meth)acrylic acid, preferably superabsorbent polymers and special polymers for leather and paper production and wastewater treatment.

The present invention further relates to a process for producing a polymer based on (meth)acrylic acid, whereby a (meth)acrylic acid according to the invention, or a purified phase, obtainable by the process according to the invention for the purification of (meth)acrylic acid, is polymerised. The polymers obtainable by this process are preferably superabsorbers, special polymers for the wastewater treatment, dispersion dye, cosmetics, textiles, leather treatment or paper production industry.

The present invention also relates to fibers, shaped articles, films, foams, superabsorbers polymers, special polymers for waste water treatment, dispersion dyes, cosmetics, textiles, leather treatment or paper production or hygiene articles, at least based on or containing (meth)acrylic acid purified according to the invention or a polymer according to the invention.

The present invention finally relates to the use of the (meth) acrylic acid produced according to the invention or a polymer according to the invention in or for the production of fibers, shaped articles, films, foams, superabsorbent polymers or hygiene articles, detergents or special polymers for the waste water treatment, dispersion dye, cosmetics, textiles, leather treatment or paper production industries.

"Superabsorbent polymers" are polymers which absorb water or aqueous fluids in a quantity which is a multiple of their inherent weight. Preferably, more than half of the superabsorbent polymers are based on acrylic acid as a monomer. Further details of superabsorbent polymers, their production and use in hygiene articles may be found in "Modern Superabsorbent Polymer Technology", Fredrick L. Buchholz, Andrew T. Graham, Wiley-VCH, 1998, the content of which will be referred to as part of this disclosure. These superabsorbent polymers are preferably incorporated into hygiene articles. Particularly preferred hygiene articles include diapers, incontinence article for adults and sanitary towels.

Furthermore, the respective combinations of features emerging from the features characterised by numerals hereinbefore represent individual embodiments of the present invention.

Further details and advantageous embodiments will be described in more detail with reference to the following drawings which will illustrate the present invention by way of examples.

FIG. 1 is a process diagram in which the process (in one stage) will be described in summary:

Stage 1
1. storage vessel
2. feed line from 1 to 3
3. suspension producer (e.g. cooling plate crystallizer, scraper cooler)
4. feed line from 3 to 5
5. wash column, hydraulic or mechanical
6. product circuit
7. product circuit pump
8. product circuit heat exchanger as melter
9. product vessel
10. product return to counter current washing wash column 5
11. mother liquor return (optional)
12. mother liquor vessel (reject)

The wash column 5, the suspension generator 3, the product circuit heat exchanger 8, the feed line 4, the product circuit 6 and the product return 10 correspond to the separating region, the crystallization region, the melter, the first guide, the second guide, the fourth or, if crystal formation takes place in the wash column, the third guide.

The melt which is to be separated and is in the liquid state, in other words controlled to a temperature just above equilibrium, is guided from the storage vessel 1 via the feed line 2 into the suspension generator 3. Crystals having a suspension packing of about 5 to about 50% (preferably, about 20 to about 30%) are formed continuously in the suspension generator 3 by cooling below the equilibrium temperature of the melt. The suspension is guided continuously through the feed line 4 into the wash column 5 where it is separated into a liquid and a solid phase by moving or stationary filters (hydraulic or mechanical (see above)). The filtrate leaves the wash column 5 and is supplied continuously to the mother liquor vessel 12. To increase the yield, at least a portion of the filtrate may optionally also be recycled via the mother liquor return 11 into the suspension generator 3.

The crystals in the wash column 5 are packed to a crystal bed and, depending on the type of wash column, are shaved off at the top or bottom by rotary blades. The shaved off product crystals are circulated as a suspension in the product circuit 6 by the circulating pump 7 and melt due to the introduction of the melt enthalpy with the melter or product heat exchanger 8.

A portion is recycled through the product return 10 into the wash column as washing fluid for counter current washing. The remainder leaves the apparatus as product in the vessel 9.

If a minimum loss of product in the reject cannot be achieved with this single-stage procedure, the mother liquor from the first stage of crystallization may optionally be worked-up in one or more further stages of crystallization or with other purification agents.

FIG. 2 shows an example of implementation in a plurality of crystallization stages.

Stage 2/3 etc.
13. mother liquor vessel from first stage (=12)
14. feed line from 13 to 15
15. suspension generator stage 2 (e.g. cooling plate crystallizer, scraper cooler)
16. feed line from 15 to 17
17. wash column, hydraulic or mechanical
18. product circuit of second stage
19. product circuit pump
20. product circuit heat exchanger as melter
22. product return to 17
23. mother liquor return to second stage crystallizer (optional)
24. mother liquor vessel of second stage (reject)
25. mother liquor supply from second stage to 26
26. suspension generator stage 3 (e.g. cooling plate crystallizer, scraper cooler)
27. supply of product from 26 to 28
28. wash column, hydraulic or mechanical
29. product circuit of third stage
30. product circuit pump
31. product circuit heat exchanger as a melter
32. product return to 28
33. mother liquor return to crystallizer of third stage (optional)
34. feed line from 28 to 35
35. mother liquor vessel (reject) of third stage
36. optional supply to further purification stages The suspension generator 15, the wash column 17, the product circuit heat exchanger 20, the feed line 16, the product circuit 18, product return 20, the mother liquor return 23 each correspond in the first apparatus unit to the crystallization region, the separating region and the melter, the first guide, the second guide, the third and fourth guide, of the second return.

The suspension generator 26, the wash column 28 and the product circuit heat exchanger 31, the product circuit 32, the product return 29, the mother liquor return 33 each correspond, in the second apparatus unit, to the crystallization region, the separating region, the melter, the second guide, the third and fourth guide of the second return.

The mother liquor feed line 25 corresponds to a connecting line.

The mother liquor (12/13) from the first stage is partially or wholly guided into the suspension generator of the second stage 15. Crystals with a suspension density of about 5 to about 50% (preferably about 20 to about 30%) are formed continuously in the suspension generator 15 by cooling below the equilibrium temperature of the melt. The suspension is guided continuously via the feed line 16 into the wash column of the second stage 17 where it is separated into a liquid and a solid phase by moving or stationary filters (hydraulic or mechanical, see above).

Once the crystals have been densified to a crystal bed, they are shaved with rotary blades at the top or bottom, depending on the type of wash column 17. The shaved off product crystals are optionally (as in the first stage) circulated as a suspension in the product circuit 18 by the circulating pump 19 and melt owing to the introduction of the melt enthalpy with the melter 20. A portion may be recycled 22 into the wash column as washing fluid for counter current washing. The remainder may be recycled into the suspension generator of the first stage 3 as a molten product. The filtrate leaves the wash column 17 and is supplied continuously to the mother liquor vessel 24. For a further increase in yield, it is optionally possible to recycle at least a portion of the filtrate also via the mother liquor return 23 into the suspension generator 15 and/or to continue working it up in a third stage.

For this purpose, the mother liquor is conveyed via 25 into a further suspension generator 26. The suspension obtained as mentioned hereinbefore is conveyed via 27 into the wash column 28 where it is packed to a crystal bed and shaved off with rotary blades at the top or bottom, depending on the type of wash column 28. The shaved off product crystals are optionally (as in the first stage) circulated as a suspension in the product circuit 29 by the circulating pump 30 and melt due to the introduction of the melt enthalpy with the heat exchanger 31.

A portion may be recycled 32 into the wash column as washing fluid for counter current washing. The remainder may be returned to the suspension generator of the first stage 3 or the second stage 15 as molten product.

Figure 3:
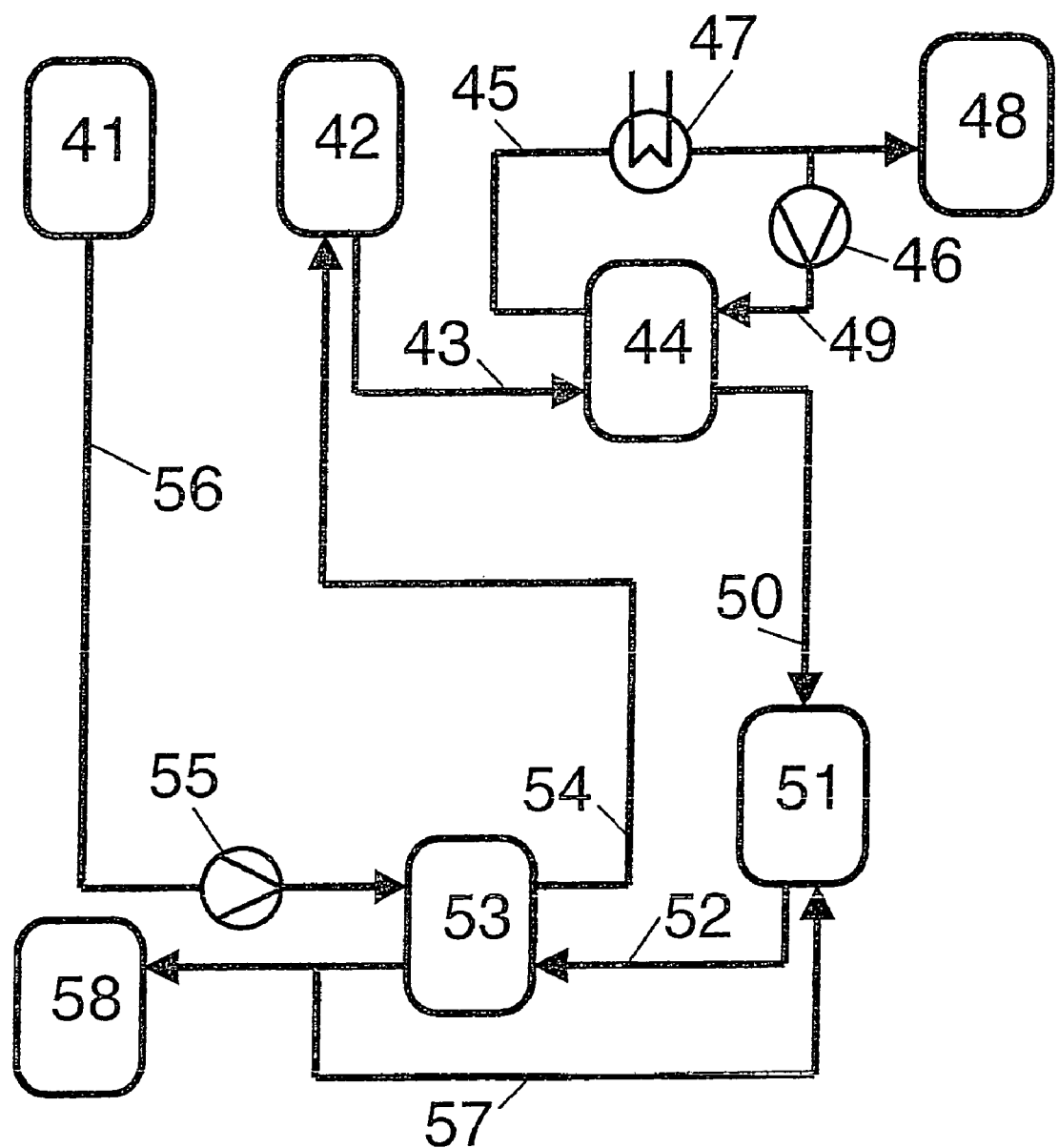
FIG. 3 is a process diagram according to the present invention with two nested process stages.

FIG. 3 shows a further preferred layout of the working up process according to the invention.
41. storage vessel
42. suspension generator (e.g. cooling plate crystallizer, scraper cooler)
43. feed line from 42 to 44
44. wash column, hydraulic or mechanical
45. product circuit
46. product circuit pump
47. product circuit heat exchanger as heat exchanger
48. product vessel
49. product return to counter current washing in wash column 44
50. feed line of the second stage equals mother liquor from stage 1 (from wash column 44)
51. suspension generator stage 2 (e.g. cooling plate crystallizer, scraper cooler)
52. feed line from 51 to 53
53. wash column, hydraulic or mechanical
54. product from the second stage (suspension, mixed with the original from 41 which is not guided in stage 1, but in stage 2) which is guided in the scraper cooler of the first stage (42)
55. product supply pump
56. supply from the first stage (41) directly to the head of the wash column 53 of the second stage
57. mother liquor return to the crystallizer of the second stage (51) (optional)
58. mother liquor vessel of the second stage (reject)

The suspension generator 42, the wash column 44, the product circuit heat exchanger 47, the product circuit 45, product return 49, the feed line 43 each correspond, in the first apparatus unit, to the crystallization region, the separating region, the separating region, the melter of the second guide, the third and fourth guide, the first guide.

The suspension generator 51, the wash column 53, the feed line 52, the mother liquor return 57 each correspond, in the second apparatus unit, to the crystallization region, the separating region, the first guide, the second return.

The feed lines 54, 50 correspond to connecting lines. The nesting shown here by way of example advantageously eliminates the need for the second apparatus unit to have a melter.

A particularly preferred variation of a two-stage or multiple-stage design guides the melt to be separated from the first stage 41 via the supply line 56 and the pump 55 to the head of the wash column of the second stage 53 where the shaved off product crystals of the second stage are guided into the suspension generator of the first stage 42 as a suspension 54. This variation has the advantage, in terms of energy, that melting in the second stage may be dispensed with and the crystals now in the first stage do not have to be frozen out again.

The counter current washing in the wash column of the second stage 53 is achieved using the melt from 41 via feed line 56 of the first stage which is very pure in comparison with the impurity concentration in the second stage and therefore allows washing which is similarly effective to washing with product.

Although a combination of a scraper cooler and a wash column is known for the production of high-purity organic substances, it could not be anticipated that this process is also very suitable for concentrating (meth)acrylic acid with starting purities of < about 99.5% by weight and with a high water content, based on the quantity of acrylic acid. It was further surprising that the content of impurities, such as further organic carbon compounds, may be considerably reduced to values by the process according to the invention. Consequently, critical variables such as furfural, inhibitors, acetic acid or maleic acid may also be depleted to uncritical values.

Figure 4:
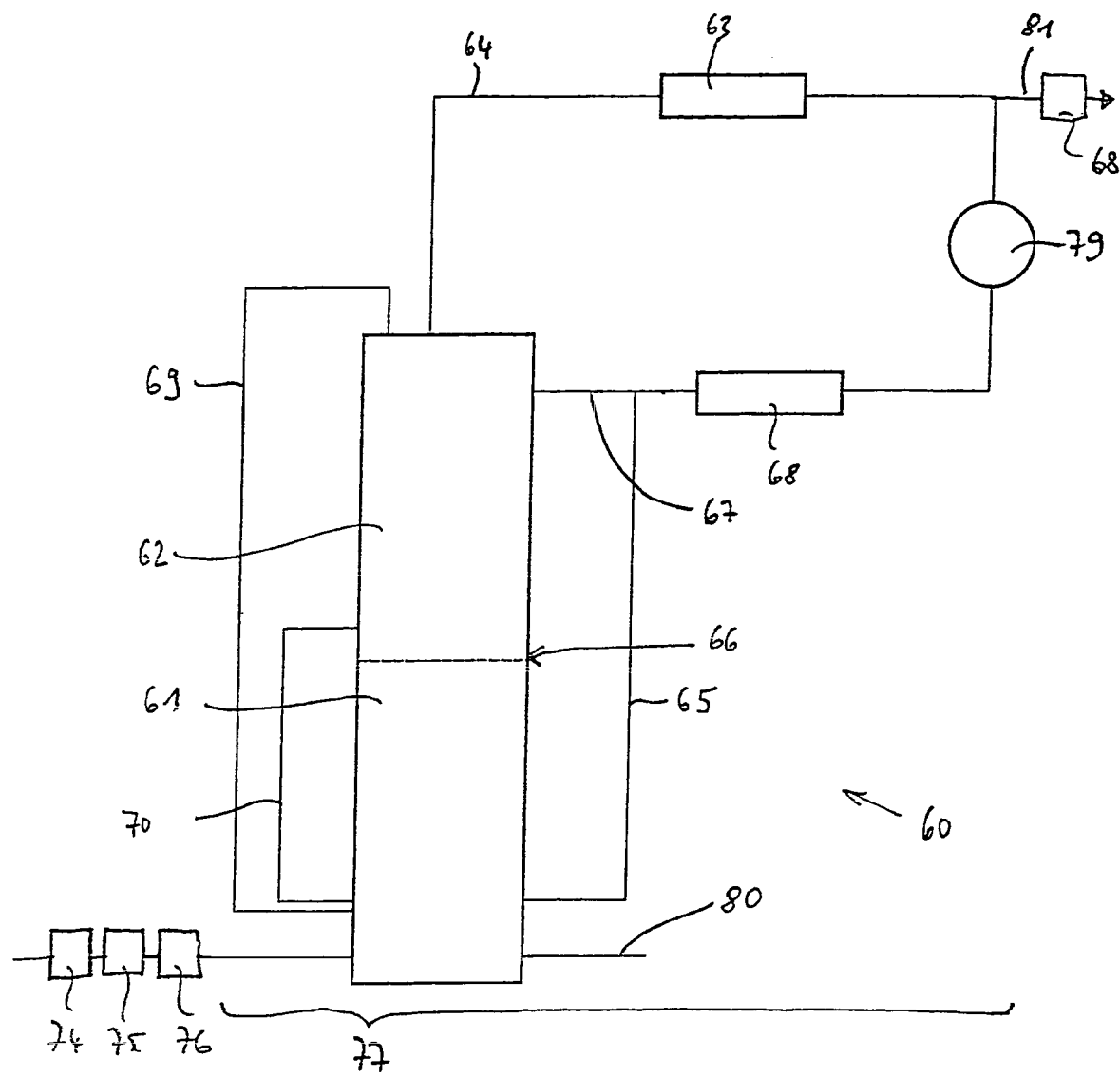
FIG. 4 is a process diagram according to the present invention with one process stage.
Figure 5:
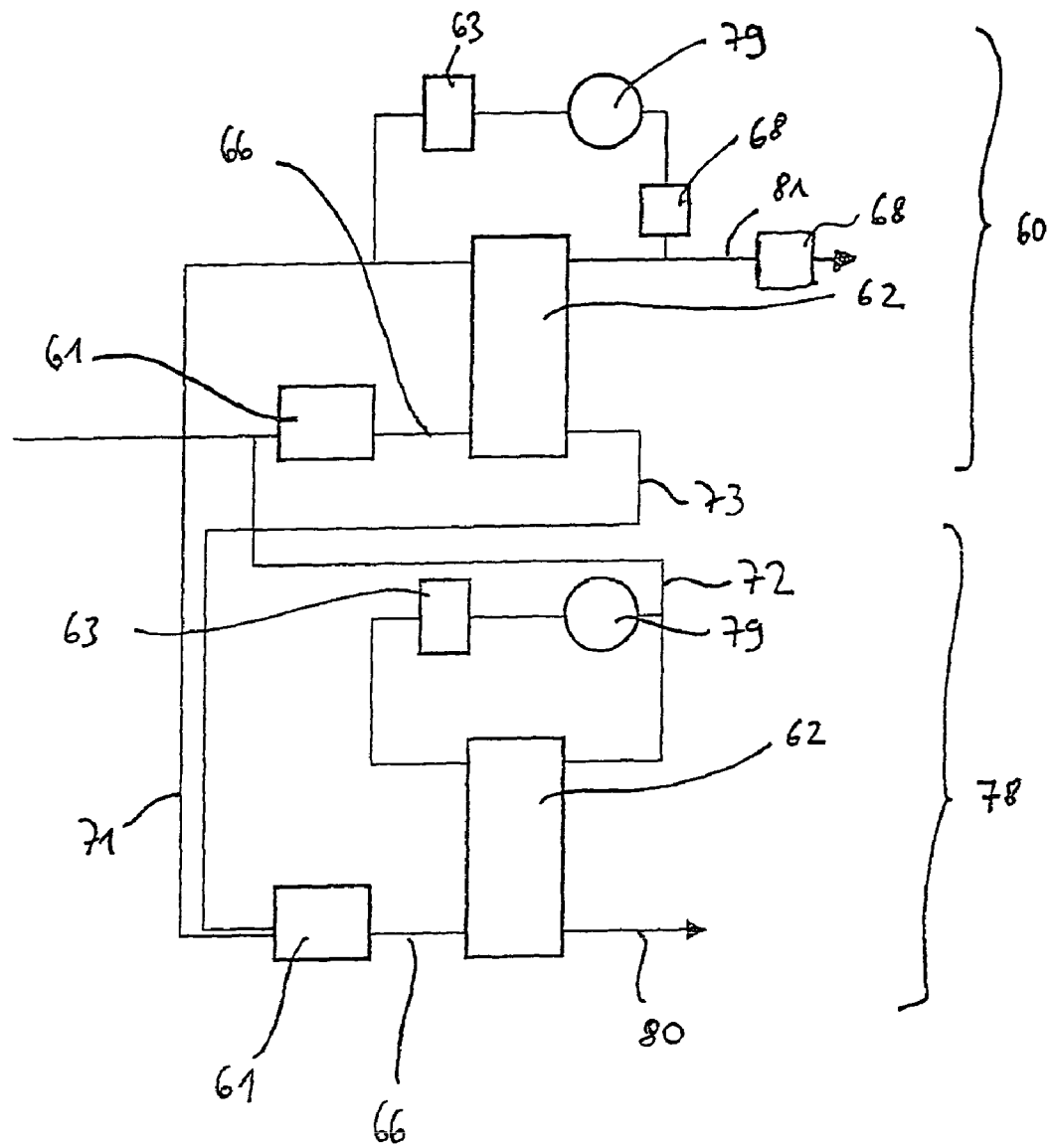
FIG. 5 is a process diagram according to the present invention with two process stages.

FIG. 4 shows a process diagram according to the invention with one process stage and FIG. 5 shows a process diagram according to the invention with two process stages.

60. apparatus unit (first process stage)
61. crystallization region
62. separating region
63. heat exchanger as melter
64. second guide
65. third guide
66. first guide
67. fourth guide
68. separate purification apparatus
69. first return
70. second return
71. connecting line
72. connecting line
73. connecting line
74. (meth)acrylic acid reactor
75. quench absorber
76. distillation apparatus
77. purification apparatus
78. apparatus unit (second process stage)
79. pump
80. residual mother liquor outlet
81. product outlet FIG. 4 shows an apparatus according to the present invention for the production of (meth)acrylic acid with a (meth)acrylic acid reactor 74, a quench absorber 75, a distillation apparatus 76 and a purification apparatus 77, the purification apparatus 77 containing a crystallization region 61 and a separating region 62. The crystallization region 61 and the separating region 62 are close together, the crystallization region 61 and the separating region 62 preferably being connected to one another directly, not by pipes. Preferably, crystal growth also takes place in a single housing during washing of the crystals, in particular separation of the crystals from the mother liquor.

The crystallization region 61 and the separating region 62 are connected to one another by a first guide 66, which may be formed by the common housing. The separating region 62 is connected via a second guide 74 to the melter 63 which melts the (meth)acrylic acid crystals separated from the mother liquor in the separation region. The molten (meth)acrylic acid is conveyed by a pump 79 either via a fourth guide 67 to the separating region 62 or via a third guide 65 to the crystallization region 61. Advantageously, a separate purification apparatus 68 has the function of increasing the purity of the (meth)acrylic acid.

To promote crystallization in the crystallization region 61, (meth)acrylic acid crystals are supplied separately as seed crystals to the crystallization region 61 by means of a first return 69 in the separating region 62. The yield is increased in that the (meth)acrylic acid remaining in the mother liquor after incomplete separation in the separating region 62 is recovered by supplying the mother liquor from the separating region 62 via a second return 70 to the crystallization region 61. The purified (meth)acrylic acid is removed from the circuit by means of a product outlet 81. Residual mother liquor which cannot be utilised is removed by means of a residual mother liquor outlet 80.

FIG. 5 shows a purification apparatus 77 with two apparatus units 60 and 78. The purification apparatus 77 comprises two process stages. In order to increase the achievable purity of the (meth)acrylic acid and the yield, the two apparatus units 60 are connected to one another by connecting lines 71, 72 and 73.

With respect to the mother liquor, which is supplied from the first apparatus unit 60 via a connecting line 73 to the second apparatus unit 78, the two apparatus units 60 and 78 are connected in series.

To increase the purity of the (meth)acrylic acid which is obtained from the second process stage with the second apparatus unit 78, which purity may be lower owing to the lower (meth)acrylic acid concentration in the mother liquor supplied to the second apparatus unit 78, the (meth)acrylic acid obtained in the second process stage is supplied to the crystallization region 61 of the first apparatus unit 60 via a connecting line 72, for further purification. Improved purity of the (meth)acrylic acid obtained is ensured by this subsequent purification.

With respect to transport of the mother liquor, the second apparatus unit 78 follows the first apparatus unit 60. With respect to transport of the (meth)acrylic acid, the first apparatus unit 60 follows the second apparatus unit 78. The two process apparatus units 78 and 60 therefore nest with one another.

Figure 6:
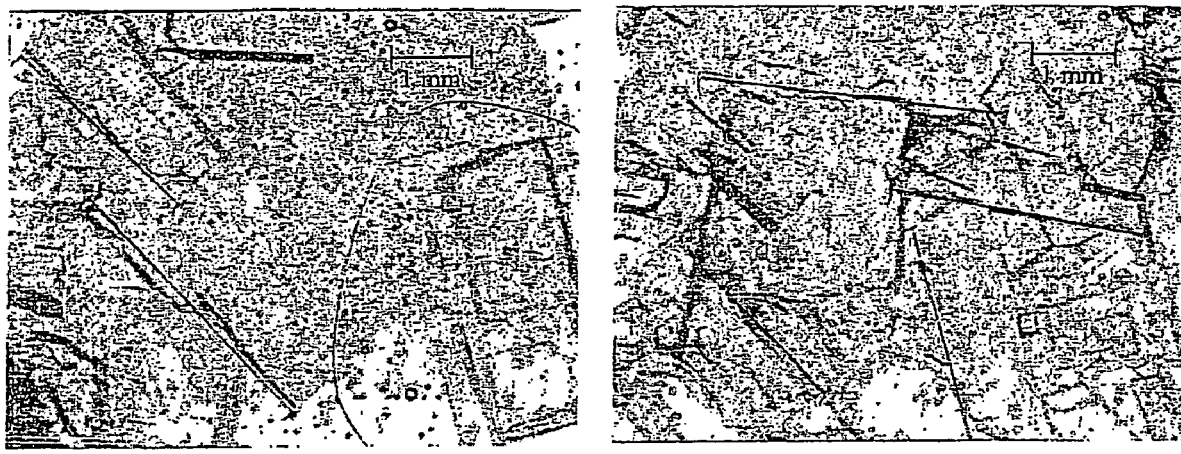
FIG. 6 shows a crystal habit of pure acrylic acid.

FIG. 6 shows a crystal habit of pure acrylic acid at an equilibrium temperature of about 12.7° C. and a crystallization temperature of about 11.25° C. with a crystallization time of about 2 hours.

Figure 7:
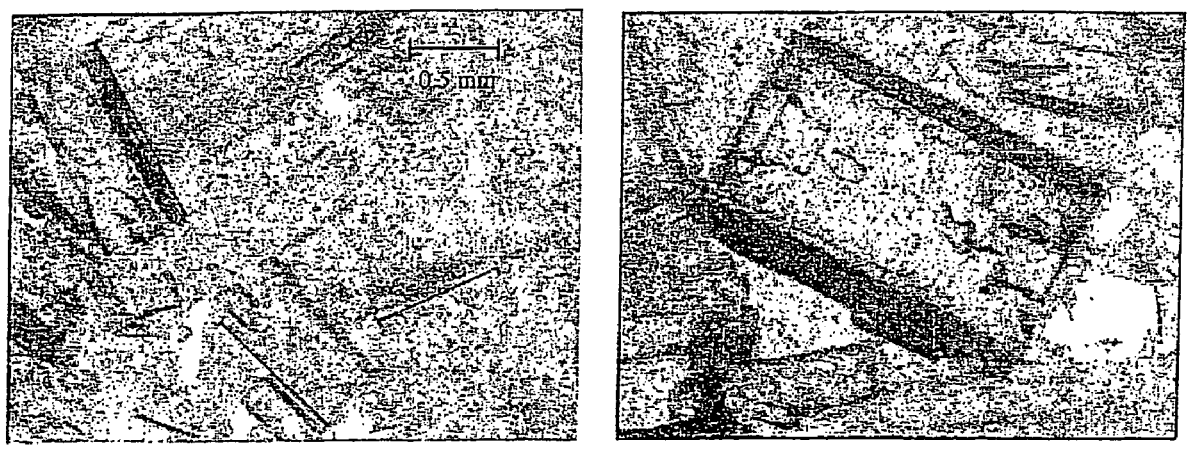
FIG. 7 shows a crystal habit according to the invention of acrylic acid from a 90/10 w/w mixture of acrylic acid and water.

FIG. 7 shows a crystal habit of acrylic acid according to the present invention from a 90/10 weight in weight (w/w) mixture of acrylic acid and water with an equilibrium temperature of about 4.5° C., with a starting temperature of about 3.1° C. and a cooling rate of about 1 K/h with a crystallization time after about 1.5 h. As the comparison of FIGS. 6 and 7 shows, the crystals according to the present invention have a small number of inclusions but that the habit changes in such a way that recesses from which mother liquor can advantageously flow appear on the respective upper side of the crystals. It can be seen that not all crystals are affected by this phenomenon.

Figure 8:
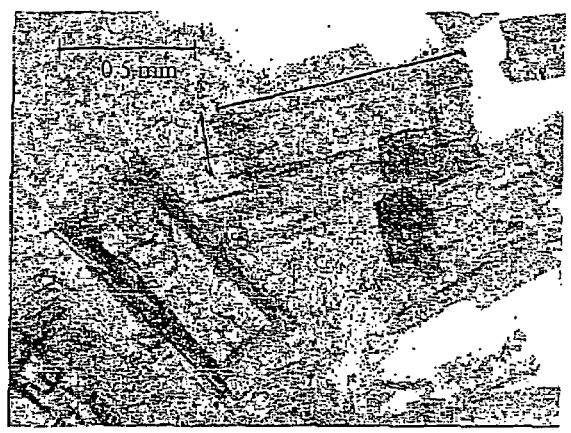
FIG. 8 shows a crystal habit according to the invention of acrylic acid from a 80/20 w/w mixture of acrylic acid and water.

FIG. 8 shows a crystal habit of acrylic acid according to the present invention consisting of a 80/20 w/w mixture of acrylic acid and water with an equilibrium temperature of about −2° C. and a starting temperature of about −3.5° C. with a cooling rate of about 1 K/h and a crystallization time of about 1.5 h. It can be seen that all crystals are affected and the size of the indentations increases.

Figure 9:
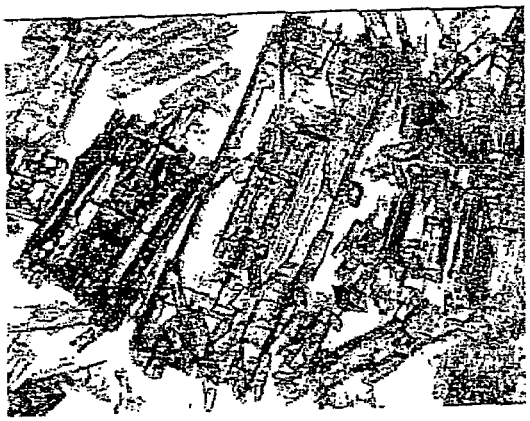
FIG. 9 shows a crystal habit according to the invention of acrylic acid from a 70/30 w/w mixture of acrylic acid and water.
Figure 9:
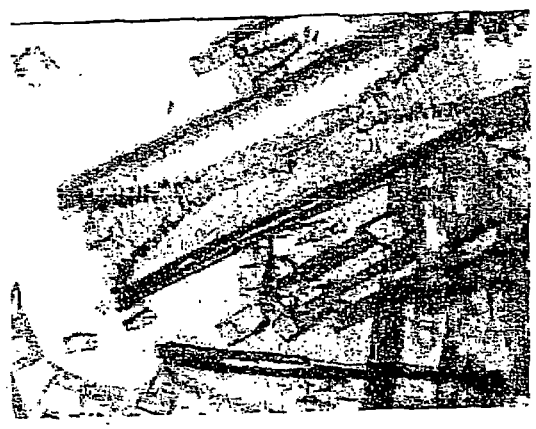

FIG. 9 shows a crystal habit of acrylic acid according to the invention consisting of a 70/30 w/w mixture of acrylic acid and water with an equilibrium temperature of about −7.5° C. and a starting temperature of about −8.7° C. with a cooling rate of about 1 K/h and a crystallization time of about 1.5 hours. FIG. 5. It can be seen that general crystal defects increase, the actual habit still being clearly discernible. Some of the recesses are so great that the crystals are internally hollow. The discharge of mother liquor is ensured and the washing out of further impurities is permitted also in this case.

The present invention will now be described in more detail with reference to non-limiting examples.

EXAMPLE I

Crystallization of Acrylic Acid Which is Depleted in Water

In an apparatus corresponding to FIG. 1 with a scraper crystallizer for suspension creation and a mechanical wash column with a piston arranged at the bottom and an outlet for the purified melt arranged at the top, acrylic acid having the following composition (Table 1) was introduced into the scraper cooler.

TABLE 1

| Name | | Starting Composition |
|---|---|---|
| Colour index | — | >700 |
| Water | % | 13.17 |
| Acetic acid | % | 1.304 |
| Furfural | % | 0.033 |
| Benzaldehyde | % | 0.038 |
| Propionic acid | % | 0.018 |
| Acrolein | % | 0.012 |
| Protoanemonine | % | 0.024 |
| Acrylic acid | % | 85.140 |
| Hydroquinone | % | 0.028 |
| Phenothiazine | % | 0.008 |
| Dimeric acrylic acid | % | 0.144 |
| Maleic acid anhydride | % | 0.276 |
| Remainder | % | — |

Acrylic acid of the composition shown in Table 1 was used as the feedstock (composition which is depleted in water).

The scraper cooler was cooled, whereby a crystal layer was formed in the scraper cooler at approximately −5° C. and shaved off by the rotary shavers in the scraper cooler to form a suspension. The filtered mother liquor was invariable sluiced completely from the process. After about 12 hours' operation, the liquid phase in the crystallizer (=filtrate from the wash column) had the composition according to Table 2.

TABLE 2

| Name | | Filtrate |
|---|---|---|
| Colour index | — | >700 |
| Water | % | 20.846 |
| Acetic acid | % | 1.855 |
| Furfural | % | 0.045 |
| Benzaldehyde | % | 0.078 |
| Propionic acid | % | 0.011 |
| Acrolein | % | 0.042 |
| Protoanemonine | % | 0.032 |
| Acrylic acid | % | 75.991 |
| Hydroquinone | % | 0.122 |
| Phenothiazine | % | 0.013 |
| Dimeric acrylic acid | % | 0.467 |
| Maleic acid anhydride | % | 0.301 |
| Remainder | % | 0.208 |

The crystal suspension removed from the crystallizer was packed in the wash column to form a compact crystal bed. On the upper side of the crystal bed, the crystal bed was shaved off using a rotary shaver, pumped in the product circuit as a crystal suspension and melted by the heat exchanger. A portion was recycled into the crystal bed for counter current washing, in order to keep the washing front constant so that neither product nor mother liquor strikes through the crystal bed. The remainder was obtained continuously as the product. The mean values from product analysis of the acrylic acid which was obtained about 1 to 3 hours later as the sample from Table 2, in other words about 12 to 15 hours after the beginning of the experiment are shown in Table 3 as examples of the product qualities achieved.

TABLE 3

| Name | | Product |
|---|---|---|
| Colour index | — | 10 |
| Water | % | 0.043 |
| Acetic acid | % | 0.182 |
| Furfural | % | <0.0001 |
| Benzaldehyde | % | <0.0001 |
| Propionic acid | % | 0.006 |
| Acrolein | % | <0.0001 |
| Protoanemonine | % | <0.0001 |
| Acrylic acid | % | 99.764 |
| Hydroquinone | % | <0.001 |
| Phenothiazine | % | <0.0001 |
| Dimeric acrylic acid | % | 0.006 |
| Maleic acid anhydride | % | <0.005 |
| Remainder | % | — |

As shown in Table 3, the process according to the invention allows the production of high-purity acrylic acid.

The concentrations were determined per GC and the colour index by the DIN-ISO 6271 method. Water was determined to ASTM D 1364 and the inhibitors (MEHQ) to ASTM D 3125.

EXAMPLE II

Crystallization of Aqueous Acrylic Acid 760 g of a sample from a quench absorber sump of an acrylic acid apparatus having a composition according to Table 4 were introduced into a stirred double shell vessel and cooled by a cryostat.

TABLE 4

| Name | | Feed |
|---|---|---|
| Water | % | 32.7 |
| Hydroquinone | % | 0.059 |
| Acetic acid | % | 3.617 |
| Furfural | % | 0.0235 |
| Benzaldehyde | % | 0.0269 |
| Propionic acid | % | 0.012 |
| Acrolein | % | 0.0101 |
| Protoanemonine | % | 0.0161 |
| Acrylic acid | % | 62.586 |
| D-acrylic acid | % | 1.088 |
| MSA | % | 0.042 |
| Remainder | % | 0.269 |
| Total minor constituents | % | 4.714 |

The sample introduced was cooled to 11° C. and then cooled further at a cooling rate of 0.1 k/min. It was inoculated with 1 mg of ice and 1 mg of crystalline acrylic acid at −15° C. The solution then became cloudy. After a further 10 minutes, the suspension was separated into solid and liquid on a vacuum filter controlled to a temperature of 0° C. with a 250 μm propyltex filter cloth. The resultant mother liquor (filtrate, 380 g) has the composition shown in Table 5. This mother liquor is more heavily depleted in acrylic acid than in water.

TABLE 5

| Name | | Filtrate |
|---|---|---|
| Water | % | 36.9 |
| Hydroquinone | % | 0.072 |
| Acetic acid | % | 3.379 |
| Furfural | % | 0.0251 |
| Benzaldehyde | % | 0.0308 |
| Propionic acid | % | 0.010 |
| Acrolein | % | 0.0113 |
| Protoanemonine | % | 0.0170 |
| Acrylic acid | % | 57.984 |
| D-acrylic acid | % | 1.047 |
| MSA | % | 0.035 |
| Remainder | % | 0.489 |
| Total minor constituents | % | 5.1162 |

Two different crystal habits (one clear white and one milky) with different melting temperatures and melting behaviour were observed on the vacuum filter. The crystals, having residual moisture of 214 g, on the vacuum filter have the composition shown in Table 6.

TABLE 6

| Name | | Crystals prior to washing (filter moist) |
|---|---|---|
| Water | % | 23.4 |
| Hydroquinone | % | 0.039 |
| Acetic acid | % | 2.364 |
| Furfural | % | 0.0161 |
| Benzaldehyde | % | 0.0183 |
| Propionic acid | % | 0.009 |
| Acrolein | % | 0.0092 |
| Protoanemonine | % | 0.0107 |
| Acrylic acid | % | 72.926 |
| D-acrylic acid | % | 0.799 |
| MSA | % | unmeasurable |
| Remainder | % | 0.409 |
| Total minor constituents | % | 3.674 |

The filter-moist crystals according to Table 6 were washed with a quantity of 200 g of VE water controlled to a temperature of 0° C. The resultant filter cake has the composition shown in Table 7.

TABLE 7

| Name | | Crystals prior to washing (filter moist) |
|---|---|---|
| Water | % | 38.8 |
| Hydroquinone | % | 0.010 |
| Acetic acid | % | 1.005 |
| Furfural | % | 0.0055 |
| Benzaldehyde | % | 0.0067 |
| Propionic acid | % | 0.004 |
| Acrolein | % | 0.0024 |
| Protoanemonine | % | 0.0037 |
| Acrylic acid | % | 59.707 |
| D-acrylic acid | % | 0.393 |
| MSA | % | 0.014 |
| Remainder | % | 0.048 |
| Total minor constituents | % | 1.493 |

The quantities specified in the foregoing were determined by gas chromatography.

In this example, a significant depletion of the by-products accompanying the aqueous acrylic acid were achieved from synthesis of the acrylic acid, as demonstrated by comparison of the total minor constituents.

The invention claimed is:

1. A process for purifying a composition comprising (meth)acrylic acid, at least one impurity and water, wherein the composition has a water content in the range of about 10 to about 85% by weight, based on the composition, to form a purified phase comprising (meth)acrylic acid and at least one impurity, wherein, in the purified phase, the quantity of at least one impurity is less than about 7 by weight, based on (meth)acrylic acid in the purified phase, comprising a stage of the process which includes the following process steps:
    a) (meth)acrylic acid is crystallized from the composition while forming a suspension comprising a mother liquor and (meth)acrylic acid crystals;
    b) (meth)acrylic acid crystals are separated from the mother liquor;
    c) at least a portion of the separated (meth)acrylic acid crystals is melted to form a melt; and
    d) a portion of the melt is recycled to step a) or step b) and wherein the portion of melt which is not recycled is in the form of a separated (meth)acrylic acid.

2. The process according to claim 1, wherein, in step a), (meth)acrylic acid crystallizes at least in part to form a crystal with a crystal structure having a surface with at least one recess located on the surface, the crystal structure having an orthorhombic Bravais crystal lattice with an Ibam space group, crystallographic data a=about 9.952 Å, b=about 11.767 Å and c=about 6.206 Å.

3. The process according to claim 1, wherein, in step a), the mother liquor comprises at least about 60% by weight of (meth)acrylic acid and water, wherein the water concentration of the mother liquor is in the range of about 10 and about 90% by weight.

4. The process according to claim 1, wherein the (meth) acrylic acid crystals are washed in the countercurrent of the recycled melt.

5. The process according to claim 1, wherein the melt is purified in a separate purification process.

6. The process according to claim 1, wherein the (meth) acrylic acid crystals from step b) are supplied at least in part to step a).

7. The process according to claim 1, wherein the mother liquor separated in step b) is recycled at least in part to step a).

8. The process according to claim 1, wherein the process comprises at least two stages, which each comprise steps a) to d), wherein at least one of the following features ($\alpha$1) to ($\alpha$4) is fulfilled:

($\alpha$1) separate (meth)acrylic acid from a first stage of the process is supplied at least in part to a second stage of the process;

($\alpha$2) separate (meth)acrylic acid from a second stage of the process is supplied at least in part to a first stage of the process;

($\alpha$3) mother liquor from a first stage of the process is supplied at least in part to a second stage of the process; and ($\alpha$4) mother liquor from a second stage of the process is supplied at least in part to a first stage of the process.

* * * * *

UNITED STATES PATENT AND TRADEMARK OFFICE
CERTIFICATE OF CORRECTION

PATENT NO. : 7,557,245 B2  Page 1 of 1
APPLICATION NO. : 10/507969
DATED : July 7, 2009
INVENTOR(S) : Stefan Nordhoff et al.

It is certified that error appears in the above-identified patent and that said Letters Patent is hereby corrected as shown below:

Column 24,
Line 35, "about 7 by weight" should read -- about 7% by weight --.

Signed and Sealed this

Twenty-fifth Day of August, 2009

David J. Kappos
*Director of the United States Patent and Trademark Office*